(12) United States Patent  (10) Patent No.: US 7,429,666 B2
Lachance et al.  (45) Date of Patent: Sep. 30, 2008

(54) PYRIDINE ANALOGS AS C5A ANTAGONISTS

(75) Inventors: Nicholas Lachance, Pierrefonds (CA); Patrick Roy, Dollard des Ormeaux (CA); Yves Leblanc, Kirkland (CA)

(73) Assignee: Merck Frosst Canada Ltd., Quebec (CA)

( * ) Notice: Subject to any disclaimer, the term of this patent is extended or adjusted under 35 U.S.C. 154(b) by 600 days.

(21) Appl. No.: 11/053,623

(22) Filed: Feb. 8, 2005

(65) Prior Publication Data

US 2005/0277644 A1    Dec. 15, 2005

Related U.S. Application Data

(60) Provisional application No. 60/578,500, filed on Jun. 10, 2004.

(51) Int. Cl.
    *C07D 215/38*    (2006.01)
(52) U.S. Cl. ..................... 546/165; 514/311; 514/314
(58) Field of Classification Search ................ 546/169; 514/311, 314
    See application file for complete search history.

(56) References Cited

FOREIGN PATENT DOCUMENTS

EP    318 140 A1    6/2003

WO    WO 03/082826 A1    10/2003
WO    WO 03/082828 A1    10/2003

OTHER PUBLICATIONS

The Journal Of Biological Chem., vol. 277, No. 51, Issue of Dec. 20, pp. 49403-49407, 2002.

*Primary Examiner*—D. Margaret Seaman
(74) *Attorney, Agent, or Firm*—Curtis C. Panzer; Valerie J. Camara

(57) ABSTRACT

The present invention provides novel compounds of Formula I which are antagonists of the C5a receptor. Compounds of the present invention are useful for the treatment of various C5a-mediated diseases and disorders; accordingly the present invention provides a method for the treatment of C5a-mediated diseases using the novel compounds described herein, as well as pharmaceutical compositions containing them.

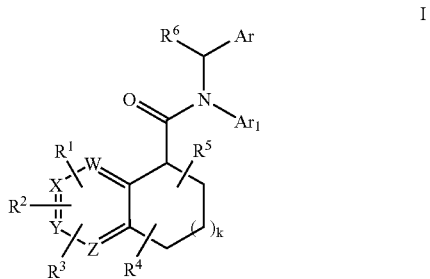

5 Claims, No Drawings

PYRIDINE ANALOGS AS C5A ANTAGONISTS

CROSS REFERENCE TO RELATED APPLICATIONS

This application claims the benefit of Provisional Application No. 60/578,500 filed Jun. 10, 2004.

BACKGROUND OF THE INVENTION

The complement system is a key component of innate immunity. It is found in the blood of mammals and is composed of over 25 proteins that recognize antibodies (immune complexes) and various pathogen surfaces which trigger a cascade of events aimed at protecting the host from "foreign" treats. During the complement activation cascade, a small peptide of 74 amino acids named C5a, is produced. This peptide has a number of biological activities including: 1) increases the permeability of small blood vessels, 2) induces the contraction of smooth muscles, 3) attracts and stimulates the pro-inflammatory activity of a variety of immune cells like macrophages, neutrophils and mast cells (reviewed by Kohl in Molecular Immunology (2001), 38:175-187). C5a mediates these effects through a G-protein coupled receptor named C5aR.

Excessive or uncontrolled complement activation can sometimes injure the host. The production of C5a is implicated in the pathogenesis of a variety of inflammatory conditions such as rheumatoid arthritis, systemic lupus erythematosus, glomerulonephritis, ischemic heart diseases, reperfusion injury, sepsis, psoriasis, atherosclerosis, inflammatory bowel diseases (IBD), adult respiratory distress syndrome (ARDS), asthma, COPD and Alzheimer's disease (reviewed by Mizuno and Morgan in Curr Drug Targets Inflamm Allergy (2004) 3:87-96 and by Kohl in Molecular Immunology (2001), 38:175-187).

Agents blocking the interaction of C5a with its receptor would be useful for treating the various inflammatory disorders driven by complement activation.

SUMMARY OF THE INVENTION

The present invention provides novel compounds of Formula I which are antagonists of the C5a receptor. Compounds of the present invention are useful for the treatment of various C5a-mediated diseases and disorders; accordingly the present invention provides a method for the treatment of C5a-mediated diseases using the novel compounds described herein, as well as pharmaceutical compositions containing them.

DETAILED DESCRIPTION OF THE INVENTION

In one aspect this application is directed to compounds of Formula I

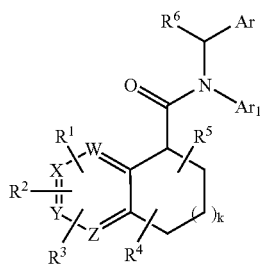

I or a pharmaceutically acceptable salts thereof, or when only one of W, X, Y and Z is —N—, the N-oxide thereof, wherein:
W, X, Y and Z are each independently selected from —CH— and —N, provided that at least one, but not more than two of W, X, Y and Z are —N—, and still further provided that when two of W, X, Y and Z are —N—, then $R^3$ is not present.

k is 0, 1, 2 or 3;

$R^1$ and $R^2$ and $R^3$ are each independently selected from the group consisting of
(1) hydrogen,
(2) —$C_{1-6}$alkyl,
(3) —$OC_{1-6}$alkyl,
(4) —$SC_{1-6}$alkyl,
(5) —$C_{2-6}$alkenyl,
(6) —$C_{3-6}$cycloalkyl,
(7) aryl,
(8) heteroaryl,
(9) heterocyclic,
(10) —$C_{1-6}$alkylaryl,
(11) —$C_{1-6}$alkylheteroaryl
(12) —$C_{1-6}$alkylheterocyclic,
(13) —O-aryl,
(14) —O-heteroaryl,
(15) —O-heterocyclic,
(16) —$OC_{1-16}$alkylaryl,
(17) —$OC_{1-6}$alkylheteroaryl
(18) —$OC_{1-6}$alkylheterocyclic,
(19) halo,
(20) —CN,
(21) —$NO_2$,
(22) —C(O)—$C_{1-6}$alkyl,
(23) —C(O)-aryl,
(24) —C(O)-heteroaryl,
(25) —C(O)-heterocyclic,
(26) —C(O)—$C_{1-6}$alkyl,
(27) —NH-$C_{1-6}$alkyl,
(28) —N($C_{1-6}$alkyl)($C_{1-6}$alkyl)
(29) —C(O)—$NH_2$,
(30) —C(O)—NH—$C_{1-6}$alkyl,
(31) —C(O)—N($C_{1-6}$alkyl)($C_{1-6}$alkyl), and
(32) $S(O)_n$—$C_{1-6}$alkyl, wherein n is 1 or 2;

wherein definitions (1) to (18) and (22) to (32) are optionally substituted with 1, 2 or 3 substituents selected from the group consisting of halo, hydroxyl, —CN, —$NO_2$, $NH_2$;

$R^4$ and $R^5$ are each independently selected from the group consisting of
(1) hydrogen,
(2) —$C_{1-6}$alkyl,
(3) —$OC_{1-6}$alkyl,
(4) —$SC_{1-6}$alkyl,
(5) —$C_{2-6}$alkenyl,
(6) —$C_{3-6}$cycloalkyl,
(7) aryl,
(8) heteroaryl,
(9) heterocyclic,
(10) —$C_{1-6}$alkylaryl,
(11) —$C_{1-6}$alkylheteroaryl
(12) —$C_{1-6}$alkylheterocyclic,
(13) —O-aryl,
(14) —O-heteroaryl,
(15) —O-heterocyclic,
(16) —$OC_{1-6}$alkylaryl,
(17) —$OC_{1-6}$alkylheteroaryl
(18) —$OC_{1-6}$alkylheterocyclic,
(19) halo,

(20) —CN,
(21) —NO₂,
(22) —C(O)—C$_{1-6}$alkyl,
(23) —C(O)-aryl,
(24) —C(O)-heteroaryl,
(25) —C(O)-heterocyclic,
(26) —C(O)—C$_{1-6}$alkyl,
(27) NH$_2$,
(28) —NH—C$_{1-6}$alkyl,
(29) —N(C$_{1-6}$alkyl)(C$_{1-6}$alkyl)
(30) —C(O)—NH$_2$,
(31) —C(O)—NH—C$_{1-16}$alkyl,
(32) —C(O)—N(C$_{1-16}$alkyl)(C$_{1-6}$alkyl),
(33) —SH, and
(34) S(O)$_n$—C$_{1-6}$alkyl, wherein definitions (1) to (18) and (22) to (32) and (34) are optionally substituted with 1, 2 or 3 substituents selected from the group consisting of halo, hydroxyl, —CN, —NO$_2$, NH$_2$;

R$_6$ is hydrogen or C$_{1-3}$alkyl, optionally substituted with 1, 2 or 3 substituents selected from
(1)-halo,
(2) —NR$^7$R$^8$,
(3) aryl,
(4) —OC$_{1-13}$alkyl,
(5) —SC$_{1-3}$alkyl, and
(6) —S(O)$_2$C$_{1-3}$alkyl,
(7) hydroxyl;

each R$_7$ and each R$_8$ are each independently hydrogen or C$_{1-3}$alkyl, optionally substituted with 1, 2 or 3 substituents selected from
(1)-halo,
(2) C$_{1-3}$alkyl,
(3) —OC$_{1-6}$alkyl,
(4) —SC$_{1-6}$alkyl,
(5) —S(O)$_2$C$_{1-6}$alkyl, Ar is aryl or heteroaryl, optionally substituted with 1, 2 or 3 substitutents selected from
(1)-halo,
(2) C$_{1-6}$alkyl, optionally substituted with 1, 2, 3 or 4 halo groups,
(3) —NR$^7$R$^8$,
(4) aryl,
(5) —OC$_{1-6}$alkyl, optionally substituted with 1, 2, 3 or 4 halo groups,
(6) —SC$_{1-6}$alkyl,
(7) —S(O)$_2$C$_{1-6}$alkyl;

Ar$_1$ is aryl or heteroaryl or C$_{3-6}$cycloalkyl, optionally substituted with 1, 2 or 3 substitutents selected from
(1)-halo,
(2) C$_{1-6}$alkyl, optionally substituted with 1, 2, 3 or 4 halo groups,
(3) —NR$^7$R$^8$,
(4) aryl,
(5) —OC$_{1-6}$alkyl, optionally substituted with 1, 2, 3 or 4 halo groups,
(6) —SC$_{1-6}$alkyl, and
(7) —S(O)$_2$C$_{1-16}$alkyl;

provided that the compound of Formula I is other than N-[4-(dimethylamino)benzyl]-N-(4-isopropylphenyl)-2-phenyl-5,6,7,8-tetrahydroquinoline-8-carboxamide.

Within this aspect there is a genus of compounds of Formula II, formula III and Formula IV:

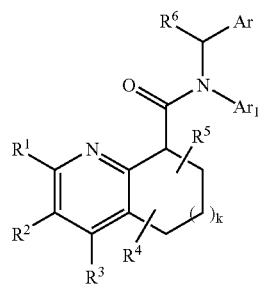

II

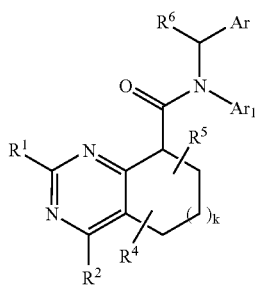

III

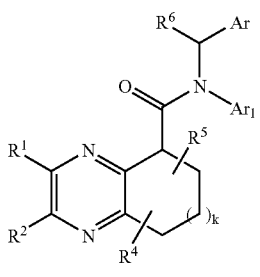

IV

Within this aspect there is a genus of compounds of Formula V, Formula VI and Formula VII:

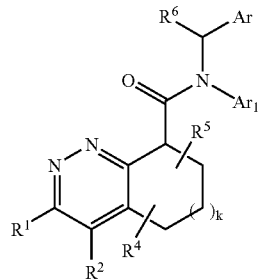

V

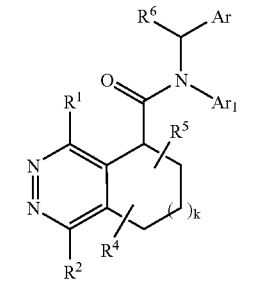

VI

-continued

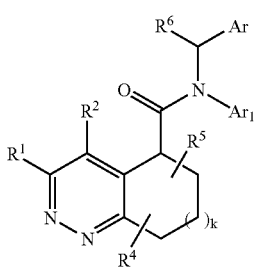
VII

Within this aspect there is a genus of pounds of Formula VIII, Formula IX and Formula X:

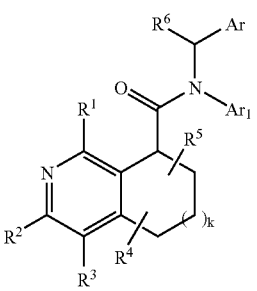
VIII

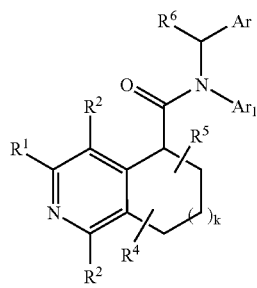
IX

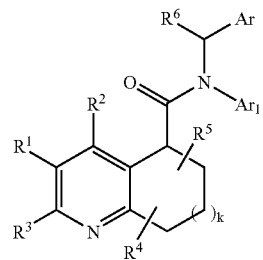
X

Within this aspect there is a genus of compounds wherein:
$R_1$ is selected from the group consisting of
(1) —$C_{1-6}$alkyl,
(2) —$OC_{1-6}$alkyl,
(3) —$SC_{1-6}$alkyl,
(4) —$C_{2-6}$alkenyl,
(5) —$C_{3-6}$cycloalkyl, wherein definitions (1) to (5) are optionally substituted with 1, 2 or 3 substituents selected from the group consisting of halo, hydroxyl, —CN, —$NO_2$, $NH_2$.

Within this aspect there is a genus of compounds wherein: $R^2$ and $R^3$ are each hydrogen.

Within this aspect there is a genus of compounds wherein: $R^4$ and $R^5$ are each hydrogen.

Within this aspect there is a genus of compounds wherein: $R^6$ is hydrogen.

Within this aspect there is a genus of compounds wherein k is 1.

Within this aspect there is a genus of compounds wherein: $R^1$ is selected from the group consisting of
(1) —$C_{1-3}$alkyl,
(2) —$OC_{1-3}$alkyl,
(3) —$SC_{1-3}$alkyl,
(4) —$C_{2-4}$alkenyl,
(5) —$C_{3-6}$cycloalkyl, wherein definitions (1) to (5) are optionally substituted with 1, 2 or 3 substituents selected from the group consisting of halo, hydroxyl, —CN, —$NO_2$, $NH_2$;
$R^2$ and $R^3$ are each hydrogen;
$R^4$ and $R^5$ are each hydrogen;
$R^6$ is hydrogen,
k is 1, and
Ar and $Ar_1$ are each independently an optionally substituted phenyl or pyridyl.

Within this aspect there is a genus of compounds of Formula II.

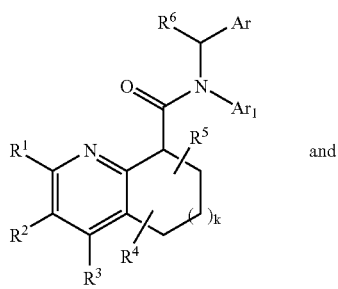
II and

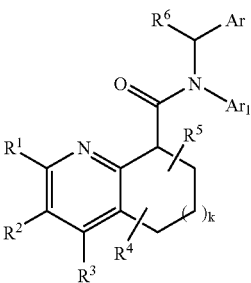
IIa

Within this genus is a class of compounds wherein:
$R^2$ and $R^3$ are each hydrogen.

Within this genus there is a class of compounds wherein: $R^4$ and $R^5$ are each hydrogen.

Within this genus there is a class of compounds wherein: $R^6$ is hydrogen.

Within this genus there is a class of compounds wherein k is 1.

Within this genus there is a class of compounds wherein: $R^1$ is selected from the group consisting of
(1) —$C_{1-3}$alkyl,
(2) —$OC_{1-3}$alkyl,
(3) —$SC_{1-3}$alkyl,
(4) —$C_{2-4}$alkenyl,
(5) —$C_{3-6}$cycloalkyl, wherein definitions (1) to (5) are optionally substituted with 1, 2 or 3 substituents selected from the group consisting of halo, hydroxyl, —CN, —$NO_2$, $N_2$;

$R^2$ and $R^3$ are each hydrogen;
$R^4$ and $R^5$ are each hydrogen;
$R^6$ is hydrogen,
k is 1, and
Ar and $Ar_1$ are each independently an optionally substituted phenyl or pyridyl.

Within this class, there is a sub-class of compounds wherein:

Ar and $Ar_1$ are each independently selected from phenyl optionally substituted with 1, 2 or 3 substituents selected from
(1) -halo,
(2) $C_{1-4}$alkyl, optionally substituted with 1, 2, 3 or 4 halo groups,
(3) —$NR^7R^8$,
(4) phenyl,
(5) —$OC_{1-4}$alkyl, optionally substituted with 1, 2, 3 or 4 halo groups,
(6) —$SC_{1-4}$alkyl; and
$R^7$ and $R^8$ are each independently hydrogen or methyl In another aspect the invention is directed to a pharmaceutical composition comprising a compound of Formula I or a pharmaceutically acceptable salt thereof; and a pharmaceutically acceptable carrier.

In another aspect the invention is directed to a method of treatment or prevention of a C5a mediated disease or disorder comprising administering to a subject in need of such treatment or prevention, a therapeutically effective amount of Formula I or a pharmaceutically acceptable salt.

Within this aspect is a genus wherein the disease or disorder is an immunoregulatory disease or disorder.

Within this aspect there is a genus wherein the disease or disorder is an inflammatory disease or disorder.

Within this aspect there is a genus wherein the disease or disorder is rheumatoid arthritis, systemic lupus erythematosus, glomerulonephritis, ischemic heart diseases, reperfusion injury, sepsis, psoriasis, atherosclerosis, inflammatory bowel diseases, adult respiratory distress syndrome, asthma, COPD and Alzheimer's disease.

Within this aspect there is a genus wherein the disease or disorder is an allergic disease, cardiac infarction, brain infarction, and serious organ injury due to activation of leukocytes caused by ischemia reperfusion, trauma, burn or surgical invasion.

In another aspect the invention is directed to a method of antagonizing C5a in a subject, comprising administering to a subject in need of such antagonism, a therapeutically effective amount of a compound of Formula I or a pharmaceutically acceptable salt.

Unless otherwise stated, the following terms have the meanings indicated below:

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "haloalkyl", such as "halo$C_{1-6}$alkyl", means alkyl substituted with one or more halo groups.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl.

The term "aryloxy" unless specifically stated otherwise includes multiple ring systems as well as single ring systems such as, for example, phenyl or naphthyl, connected through the oxy connecting atom to the connecting site.

Ther term "$C_0$-$C_6$alkyl" includes alkyls containing 6, 5, 4, 3, 2, 1, or no carbon atoms. An alkyl with no carbon atoms is a hydrogen atom substituent or a direct bond—depending on whether the alkyl is a terminus or a bridging moiety.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Examples of heterocyclo$C_{3-7}$alkyl include, for example, azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

Examples of aryl($C_{1-6}$)alkyl include, for example, phenyl ($C_{1-6}$)alkyl, and naphthyl($C_{1-6}$)alkyl.

Examples of heterocyclo$C_{3-7}$alkylcarbonyl($C_{1-6}$)alkyl include, for example, azetidinyl carbonyl($C_{1-6}$)alkyl, pyrrolidinyl carbonyl($C_{1-6}$)alkyl, piperidinyl carbonyl($C_{1-6}$)alkyl, piperazinyl carbonyl($C_{1-6}$)alkyl, morpholinyl carbonyl($C_{1-6}$) alkyl, and thiomorpholinyl carbonyl($C_{1-6}$)alkyl.

The term "amine" unless specifically stated otherwise includes primary, secondary and tertiary amines.

Unless otherwise stated, the term "carbamoyl" is used to include —NHC(O)OC$_1$-C$_4$alkyl, and —OC(O)NHC$_1$-C$_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl(C$_{1-6}$)alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Prodrugs

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The following are examples of representative pharmaceutical dosage forms for the compounds of Formula I:

| Injectable Suspension (I.M.) | mg/mL |
|---|---|
| Compound of Formula I10 | |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I25 | |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
| --- | --- |
| Compound of Formula I25 | |
| Lactose Powder | 573.5 |
| Magnesium Stearate | 1.5 |
| | 600 |

Utilities

Compounds described in this invention are antagonists of the C5a receptor. The ability of the compounds described in this invention to interact with the C5a receptor makes them useful for preventing or reversing undesirable symptoms caused by C5a in a mammalian, especially human subject. The antagonism of the actions of C5a indicates that the compounds and pharmaceutical compositions thereof are useful to treat, prevent, or ameliorate in mammals and especially in humans: respiratory conditions, allergic conditions, inflammatory conditions, neurodegenerative conditions as well as immune and autoimmune diseases.

Accordingly, another aspect of the invention provides a method of treating or preventing a C5a mediated disease comprising administering to a mammalian patient in need of such treatment a compound described in this invention in an amount which is effective for treating or preventing said C5a-mediated disease. C5a-mediated diseases include, but are not limited to rheumatoid arthritis, systemic lupus erythematosus, glomerulonephritis, ischemic heart diseases, reperfusion injury, sepsis, psoriasis, atherosclerosis, inflammatory bowel diseases (IBD), adult respiratory distress syndrome (ARDS), asthma, chronic obstructive pulmonary disease (COPD) and Alzheimer's disease.

Assay for the Evaluation of Biological Activity

Compounds of Formula I can be tested using the following assays to determine their antagonist or agonist activity in vitro.

C5a Receptor Competitive Binding Assay

The full length coding sequence of C5a receptor (C5aR) is subcloned into the appropriate site of a mammalian expression vector and transfected into rat basophilic leukemia (RBL) cell line-2H3. The RBL cells expressing the C5aR are grown under selection, individual colonies are isolated after 2-3 weeks of growth and subsequently expanded into clonal cell lines.

A selected clonal RBL cell line expressing the C5aR is maintained in culture and harvested. Membranes are collected by differential centrifugation following lysis of the cells by nitrogen cavitation in the presence of protease inhibitors. To a test mixture comprising 0.25 μg of membranes mixed with 70 μM of $^{125}$I-C5a (Specific activity: 2200 Ci/mMole; from Perkin Elmer) in 75 μl of assay buffer (Hanks Balanced Salt buffered Saline with 10 mM Hepes containing 0.25% bovine serum albumin) a test compound is added at concentrations ranging from 0.1 nM to 10 μM. After a 90 minutes incubation at room temperature, the test mixture is filtered using a TOMTEC harvester over Packard GF/C filters (or equivalent) and the filter washed using 50 mM MES, pH 5.5 wash buffer. The non-specific background is measured by the addition of 35 nM of unlabelled C5a (from Calbiochem) to the test mixture in the absence of the test compound.

Whole Cell Assays to Determine C5a Receptor Agonists and Antagonists

I. Enzyme Release Assay

In order to increase the expression of C5aR the monocytic cell line U937 is differentiated by incubating the cells in the presence of 1 mM dibutyryl cAMP for 72 hours. The differentiated U937 cells (dU937) are harvested and resuspended in the assay buffer (Hank's balanced salt solution+10 mM Hepes+0.25% bovine serum albumin) and 125,000 cells per well are distributed onto Millipore multiscreen 1.2% durapore plates. The dU937 cells are then stimulated for 3 minutes at 37° C. in presence of 10 nM C5a in the assay buffer described above. The presence of C5a in this assay causes the release of the lysosomal enzyme N-acetyl-β-D-glucosaminidase from the cells into the assay buffer. At the end of the stimulation, the assay buffer is separated from the cells by applying vacuum to the multiscreen plates. The amount of enzyme released in the assay buffer is determined by a simple colorimetric assay. To the assay buffer, 8 mM of 4-nitrophenyl N-acetyl-β-D-glucosaminide substrate is added and incubated for 90 minutes at 37° C. The reaction is quenched with the addition of a 1:5 dilution of a stop buffer (1.2M glycine/NaoH pH 10.4), the color developed is determined at an absorbance of 405 nm. To evaluate the antagonist activity, the test compound is pre-incubated at concentrations ranging from 0.1 nM to 2 μM with the cells for 20 minutes at 37° C. prior to the addition of C5a. To determine if the test compound has agonist activity, the compound is added to the cells at a concentration of 10 μM for 3 minutes at 37° C.

II Calcium Mobilization Assay

RBL clonal cells expressing the C5aR are plated at 45,000 cells per well in a 96-well plate and incubated 24 hours prior to the assay. Into each well, 100 ul of the cytoplasmic calcium indicator (no wash dye from Molecular Devices) is added and the plates are incubated for an additional 45 minutes at 37° C. Changes in cell fluorescence are monitored before and after the addition of 2 nM C5a using a FLIPR™ (Molecular Devices) at $\lambda_{ex}$=488 nm and $\lambda_{em}$=540 nm. To determine the antagonist activity, the test compound is pre-incubated at concentrations ranging from 0.01 nM to 10 μM with the cells for 10 minutes at 37° C. prior to the addition of C5a. To determine if the test compound has agonist activity, the compound is added to the cells at a concentration of 10 μM and changes in fluorescence monitored.

Determination of Ligand Agonist Activity Microphysiometry

The assay measures the change in the acidification in the cell media when a ligand binds to a C5aR, activating cellular metabolism. Briefly, RBL clonal cells expressing the C5aR are incubated overnight at 37° C. in a Cytosensor cell capsule cup (Molecular Devices). The cup is placed in the sensor chamber of the microphysiometer (Molecular Devices). The sensor monitors the voltage change in the chamber, which is proportional to the concentration of H$^+$ ions produced as a result of increased cellular metabolism. Cells are exposed to various concentrations of a test compound and an increase in the rate of voltage change in the chamber indicates agonist activity.

C5a Receptor Antagonist Whole Blood Assay

The assay is based on the capacity of exogenous C5a to stimulate the release of IL-6 in human or primate whole blood.

Blood collected into tubes containing an anti-coagulant (heparin; 14 U/ml blood) is pre-incubated in the presence of a carboxypeptidase N inhibitor at a final concentration of 100 nM at 37° C. for 15 minutes (carboxypeptidase N inhibitor prevents the removal of the carboxy-terminal arginine on C5a by proteases in the blood which is necessary for optimal activity of the ligand). C5a is then added to a final concentration of 45 nM and the blood is incubated at 37° C. for 24 hours. The blood is then centrifuged at 1500 g for 15 minutes at 4° C. and the amount of IL-6 in the plasma is determined by ELISA (from BioSouce). To determine the antagonist activity, the test compound is pre-incubated with the carboxypeptidase N inhibitor for 15 minutes at 37° C. at concentrations ranging from 0.001 nM to 10 µM prior to the addition of C5a.

The invention will now be illustrated in the following non-limiting Examples in which, unless otherwise stated:
1. All the end products of the formula I were analyzed by NMR, TLC.
2. Intermediates were analyzed by NMR and/or TLC.
3. Most compounds were purified by flash chromatography on silica gel, recrystallization and/or swish (suspension in a solvent followed by filtration of the solid).
4. The course of reactions was followed by thin layer chromatography (TLC) and reaction times are given for illustration only.

The following intermediates were prepared according to literature procedures or purchased from the following vendor:

5,6,7,8-Tetrahydroquinolin-2 (1H)-one: (a) Cappelli, A.; Anzini, M.; Vomero, S.; Mennuni, L.; Makovec, F.; Doucet, E.; Hamon, M.; Bruni, G.; Romeo, M. R.; Menziani, M. C.; De Benedetti, P. G.; Langer, T. J. Med. Chem. 1998; 41, 728-741. (b) Meyers, A. I.; Garcia-Munoz, G. J. Org. Chem. 1964; 29, 1435-1438.

1,5,6,7-Tetrahydro-2H-cyclopenta[b]pyridin-2-one: Cappelli, A.; Anzini, M.; Vomero, S.; Mennuni, L.; Makovec, F.; Doucet, E.; Hamon, M.; Bruni, G.; Romeo, M. R.; Menziani, M. C.; De Benedetti, P. G.; Langer, T. J. Med. Chem. 1998; 41, 728-741.

2-Methyl-5,6,7,8-tetrahydroquinoline: TCI

2-Chloro-5,6,7,8-tetrahydroquinoline: Zimmerman, S. C.; Zeng, Z; Wu, W.; Reichert, D. E. J. Am. Chem. Soc. 1991; 113, 183-196.

Method A

An appropriately substituted benzaldehyde 1 is reductively animated with aniline 2 using a reducing agent such as NaB(OAc)$_3$H to give the corresponding N-benzylaniline 3.

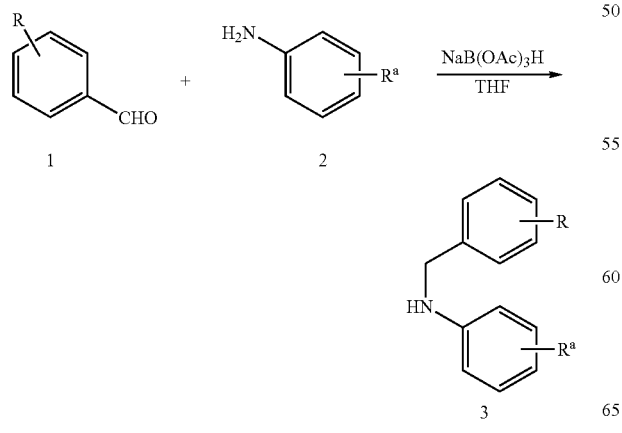

Method B

Pyridine-2-one 4 (ref. 1, 2) is alkylated with an alkyl iodide R$^b$I and a suitable silver salt such as Ag$_2$CO$_3$ to give alkoxypyridine 5. Treatment with a strong base such as t-BuLi in THF or Et$_2$O gives the anion which is quenched with CO$_2$ (g). After removal of the solvent, the intermediate lithium carboxylate and an appropriate amine 3 are treated with a suitable coupling reagent such as T3P and a suitable base such as N-methylmorpholine in DMG to give the corresponding amide 6.

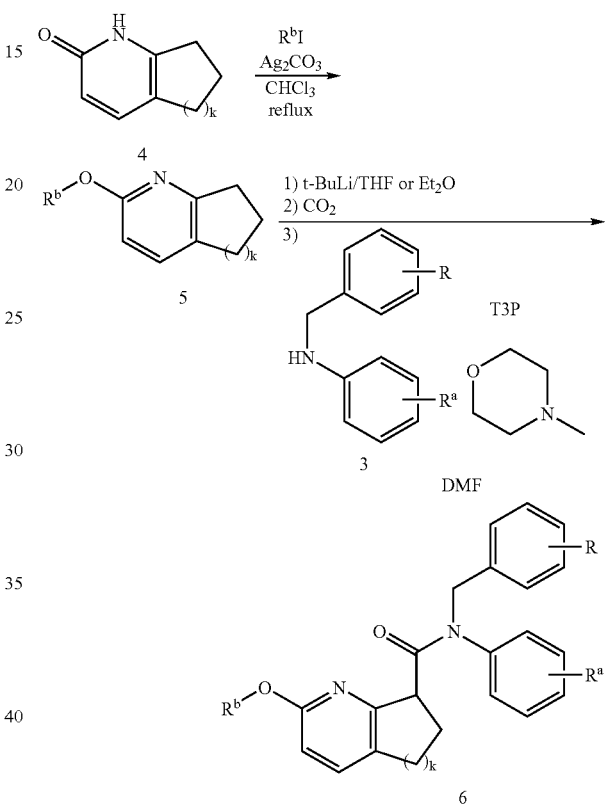

k = 1, 2, 3

Method C

Quinaldine is treated with a suitable strong base such as LDA and an alkylating agent R$^c$X to give alkylquinoline 8. Hydrogenation over a suitable catalyst such as PtO$_2$ in a solvent such as TFA overnight gives pyridine 9. Treatment with a strong base such as t-BuLi in THF or Et$_2$O gives the anion which is quenched with CO$_2$ (g). After removal of the solvent, the intermediate lithium carboxylate and an appropriate amine 3 are treated with a suitable coupling reagent such as T3P and a suitable base such as N-methylmorpholine in DMF to give the corresponding amide 10.

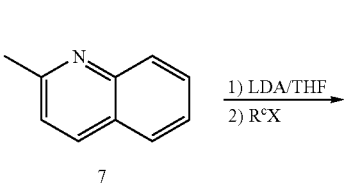

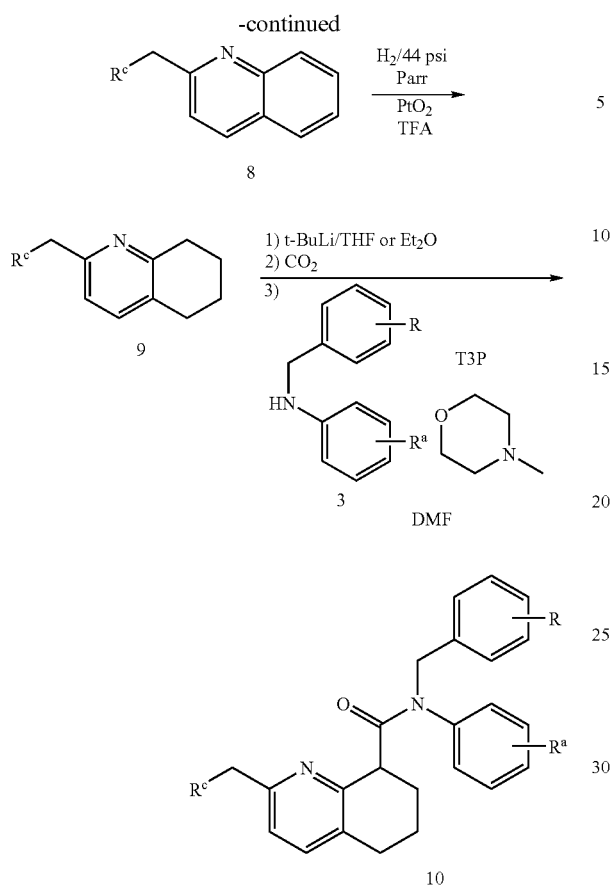

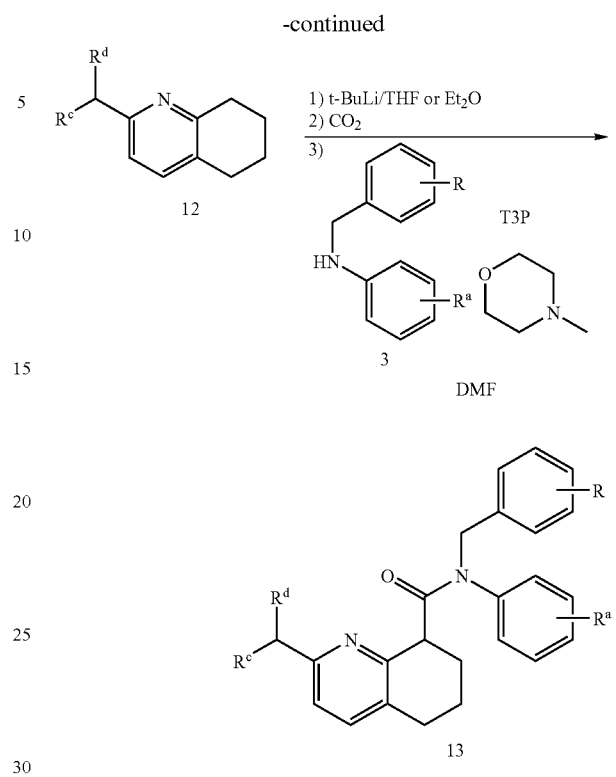

Method D

Alkylquinoline 8 is treated with a suitable strong base such as LDA and an alkylating agent $R^dX$ to give alkylquinoline 11. Hydrogenation over a suitable catalyst such as $PtO_2$ in a solvent such as TFA overnight gives pyridine 12. Treatment with a strong base such as t-BuLi in THF or $Et_2O$ gives the anion which is quenched with $CO_2$ (g). After removal of the solvent, the intermediate lithium carboxylate and an appropriate amine 3 are treated with a suitable coupling reagent such as T3P and a suitable base such as N-methylmorpholine in DMF to give the corresponding amide 13.

Method E

2-Halocycloalkylpyridine 14 is treated with an alkyl thiolate in NMP to give thioether 15. Treatment with a strong base such as t-BuLi in THF or $Et_2O$ gives the anion which is quenched with $CO_2$ (g). After removal of the solvent, the intermediate lithium carboxylate and an appropriate amine 3 are treated with a suitable coupling reagent such as T3P and a suitable base such as N-methylmorpholine in DMF to give the corresponding amide 16.

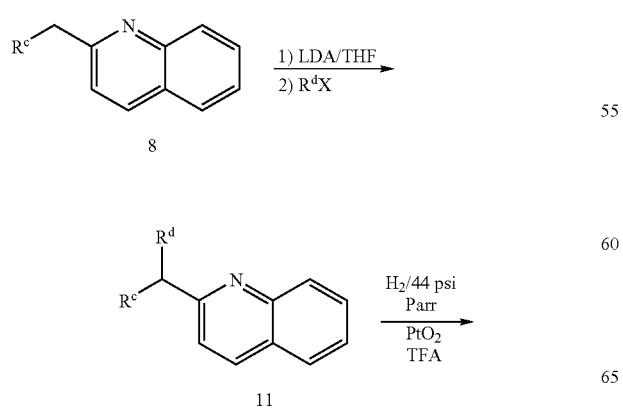

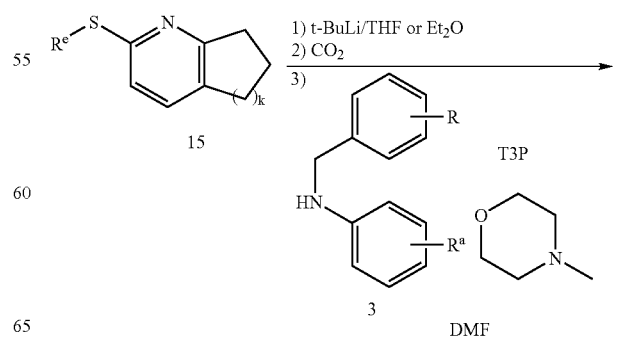

-continued

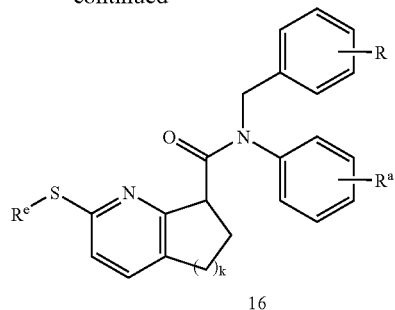

k = 1, 2, 3

EXAMPLE 1A (+) or (−)-N-[4-(Dimethylamino)benzyl]-N-(4-isopropylphenyl)-2-methoxy-5,6,7,8-tetrahydroquinoline-8-carboxamide (Enantiomer A)

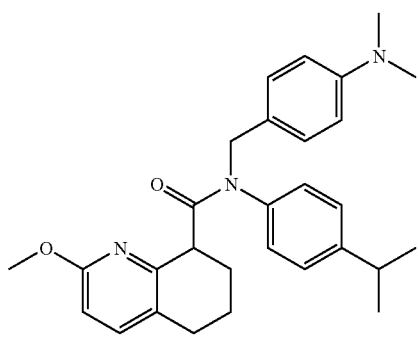

Step 1.
N-[4-(Dimethylamino)benzyl]-4-isopropylaniline

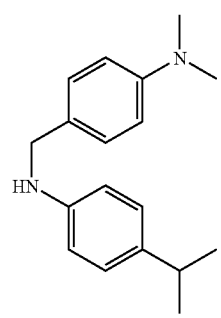

To a 0.33 M solution of 4-(dimethylamino)benzaldehyde in THF at 0° C. was added 1.1 equiv of 4-isopropylaniline followed by 1.5 equiv of sodium triacetoxyborohydride. After allowing the reaction to warm to room temperature overnight, this mixture was poured into a separatory funnel containing aqueous NH₄Cl/EtOAc. The organic layer was washed with brine, dried over anhydrous Na₂SO₄, filtered and concentrated. The crude material was further purified by flash chromatography, eluting with a gradient from 100% hexanes to 10% EtOAc/hexanes to provide the title compound as a white solid.

¹H NMR (acetone-d₆) δ 7.23 (2H, d), 6.97 (2H, d), 6.73 (2H, d), 6.61 (2H, d), 5.03 (1H, br s), 4.19 (2H, d), 2.91 (6H, s), 2.76 (1H, m), 1.17 (6H, d).

Step 2. 2-Methoxy-5,6,7,8-tetrahydroquinoline

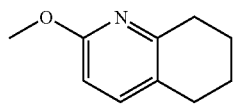

To a 0.33 M solution of 5,6,7,8-tetrahydroquinolin-2 (1H)-one in dry CHCl₃ at room temperature was added 1.2 equiv of Ag₂CO₃ and 6 equiv of MeI. The final suspension was refluxed in the dark for 5 h. After allowing the reaction to cool to room temperature, the suspension was filtered through Celite and concentrated. The crude material was further purified by flash chromatography, eluting with a gradient from 100% hexanes to 10% EtOAc/hexanes to provide the title compound as a colorless oil.

¹H NMR (acetone-d₆) δ 7.32 (1H, d), 6.50 (1H, d), 3.83 (3H, s), 2.74 (2H, m), 2.67 (2H, m), 1.84 (2H, m), 1.78 (2H, m).

Step 3. (+/−)-N-[4-(Dimethylamino)benzyl]-N-(4-isopropylphenyl)-2-methoxy-5,6,7,8-tetrahydroquinoline-8-carboxamide

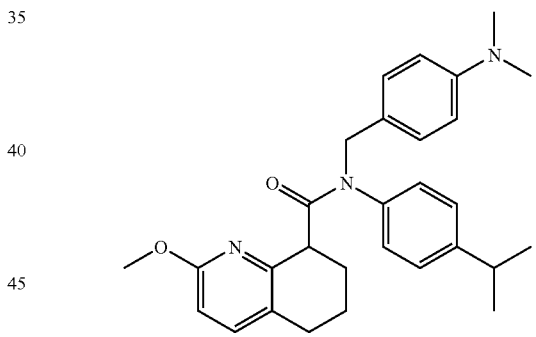

To a 0.22 M solution of 2-methoxy-5,6,7,8-tetrahydroquinoline in Et₂O at −78° C. was added 1.7 equiv of t-BuLi [1,7M] over 5 min. After allowing the reaction to warm up to 0° C. and stirring at this temperature for 30 min, a stream of CO₂(g) was then allowed to flow into the flask. The final mixture was allowed to warm to room temperature and the solvent was removed by the flow of CO₂. To a solution/suspension of the resulting crude lithium carboxylate salt in DMF (12 equiv) at 0° C. was successively added 1.2 equiv of N-[4-(dimethylamino)benzyl]4-isopropylaniline, 12 equiv of 4-methylmorpholine and 4.0 equiv of 1-propylphosphonic acid cyclic anhydride (50% in EtOAc). After allowing the reaction to warm to room temperature overnight, this mixture was poured into a separatory funnel containing aqueous NaHCO₃/EtOAc. The organic layer was washed with brine, dried over anhydrous MgSO₄, filtered and concentrated. The crude material was further purified by flash chromatography, eluting with a gradient from 100% hexanes to 25% EtOAc/hexanes to provide the title compound as a white solid.

¹H NMR (acetone-d₆) δ 7.36-7.31 (3H, m), 7.28 (2H, d), 7.14 (2H, d), 6.65 (2H, d), 6.53 (1H, d), 5.20 (1H, d), 4.51 (1H, d), 3.87-3.82 (4H, m), 2.95-2.88 (7H, m), 2.71 (1H, m), 2.58 (1H, m), 2.08-2.02 (2H, m), 1.94 (1H, m), 1.46 (1H, m), 1.23 (6H, d).

Step 4. (+) or (−)-N-[4-(Dimethylamino)benzyl]-N-(4-isopropylphenyl)-2-methoxy-5,6,7,8-tetrahydroquinoline-8-carboxamide (Enantiomer A)

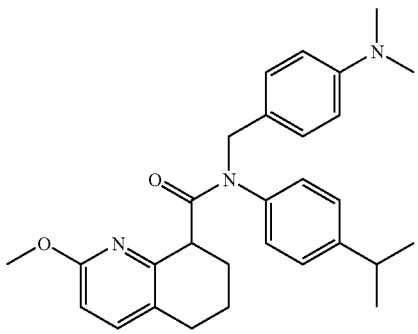

The enantiomers were then separated on a Chiralcel OD column (2×25 cm) eluting with 1:10 isopropanol:hexane at a flow rate of 6 mL/min and a wavelength of 254 nm. The first eluting isomer (Example 1A) had a retention time of 24.0 min, and the second eluting isomer (Example 1B) had a retention time of 31.6 min.

¹H NMR (acetone-d₆) δ 7.36-7.31 (3H, m), 7.28 (2H, d), 7.14 (2H, d), 6.65 (2H, d), 6.53 (1H, d), 5.20 (1H, d), 4.51 (1H, d), 3.87-3.82 (4H, m), 2.95-2.88 (7H, m), 2.71 (1H, m), 2.58 (1H, m), 2.08-2.02 (2H, m), 1.94 (1H, m), 1.46 (1H, m), 1.23 (6H, d).

EXAMPLE 1B (−) or (+)-N-[4-(Dimethylamino)benzyl]-N-(4-isopropylphenyl)-2-methoxy-5,6,7,8-tetrahydroquinoline-8-carboxamide (Enantiomer B)

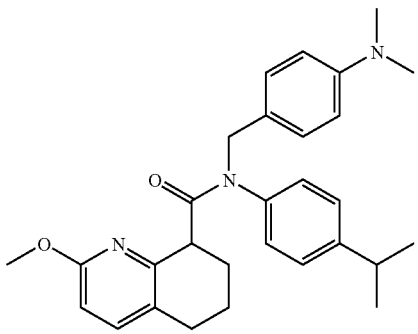

The title compound was obtained as the second eluting isomer (retention time of 31.6 min) from the chromatography described in Example 1A, Step 4.

¹H NMR (acetone-d₆) δ 7.36-7.31 (3H, m), 7.28 (2H, d), 7.14 (2H, d), 6.65 (2H, d), 6.53 (1H, d), 5.20 (1H, d), 4.51 (1H, d), 3.87-3.82 (4H, m), 2.95-2.88 (7H, m), 2.71 (1H, m), 2.58 (1H, m), 2.08-2.02 (2H, m), 1.94 (1H, m), 1.46 (1H, m), 1.23 (6H, d).

EXAMPLE 2

(+/−)-N-[4-(Dimethylamino)benzyl]-N-(4-isopropylphenyl)-2-methoxy-6,7-dihydro-5H-cyclopenta[b]pyridine-7-carboxamide

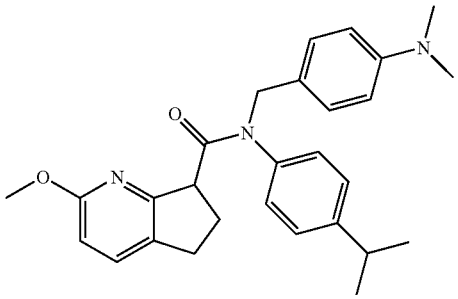

Step 1. 2-Methoxy-6,7-dihydro-5H-cyclopenta[b]pyridine

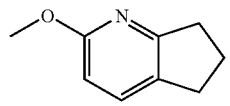

Following the procedure described in Example 1A, step 2, 1,5,6,7-tetrahydro-2H-cyclopenta[b]pyridin-2-one and MeI gave the title compound as a colorless oil.

¹H NMR (CDCl₃) δ 7.37 (1H, d), 6.47 (1H, d), 3.90 (3H, s), 2.91 (2H, t), 2.82 (2H, t), 2.09 (2H, quint).

Step 2. (+/−)-N-[4-(Dimethylamino)benzyl]-N-(4-isopropylphenyl)-2-methoxy-6,7-dihydro-5H-cyclopenta[b]pyridine-7-carboxamide

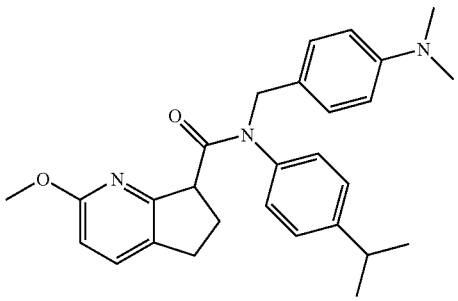

Following the procedure described in Example 1A, step 3, using 2-methoxy-6,7-dihydro-5H-cyclopenta[b]pyridine, and N-[4-(dimethylamino)benzyl]-4-isopropylaniline gave the title compound as a colorless oil.

¹H NMR (acetone-d₆) δ 7.50 (1H, d), 7.43 (2H, m), 7.27 (2H, d), 7.15 (2H, d), 6.66 (2H, d), 6.57 (1H, d), 5.30 (1H, d), 4.49 (1H, d), 4.05-4.02 (1H, m), 3.94 (3H, s), 3.00-2.89 (8H, m), 2.72 (1H, m), 2.51 (1H, m), 2.16 (1H, m), 1.22 (6H, d).

EXAMPLE 3

(+/−)-N-(4-Chlorobenzyl)-N-(4-isopropylphenyl)-2-methoxy-5,6,7,8-tetrahydroquinoline-8-carboxamide

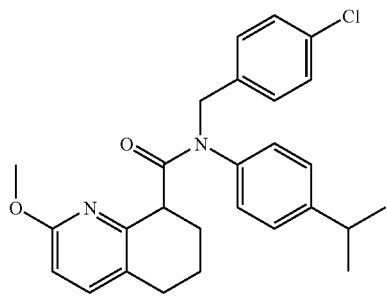

Step 1. N-(4-Chlorobenzyl)-4-isopropylaniline

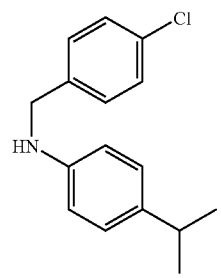

Following the procedure described in Example 1A, step 1, 4-chlorobenzaldehyde and 4-isopropylaniline gave the title compound as an off-white solid.

$^1$H NMR (acetone-$d_6$) δ 7.43 (2H, d), 7.35 (2H, d), 6.98 (2H, d), 6.58 (2H, d), 5.38 (1H, br s), 4.35 (2H, d), 2.75 (1H, m), 1.17 (6H, d).

Step 2. (+/−)-N-(4-Chlorobenzyl)-N-(4-isopropylphenyl)-2-methoxy-5,6,7,8-tetrahydroquinoline-8-carboxamide

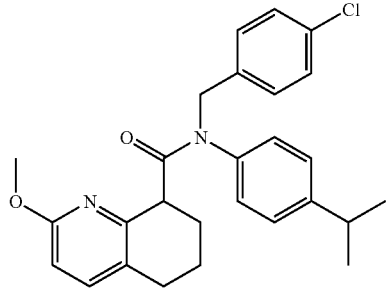

Following the procedure described in Example 1A, step 3, using 2-methoxy-5,6,7,8-tetrahydroquinoline, and N-(4-chlorobenzyl)-4-isopropylaniline gave the title compound as a foam.

$^1$H NMR (acetone-$d_6$) δ 7.41-7.30 (9H, m), 6.55 (1H, d), 5.32 (1H, d), 4.62 (1H, d), 3.91-3.86 (4H, m), 2.92 (1H, sept), 2.71 (1H, m), 2.59 (1H, m), 2.10-1.94 (3H, m), 1.46 (1H, m), 1.22 (6H, d).

EXAMPLE 4

(+/−)-N-(4-Isopropylbenzyl)-N-(4-isopropylphenyl)-2-methoxy-5,6,7,8-tetrahydroquinoline-8-carboxamide

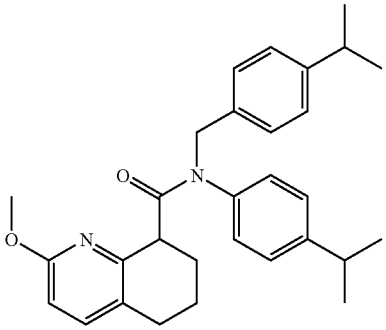

Step 1. (4-Isopropylbenzyl)(4-isopropylphenyl)amine

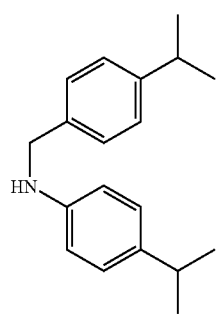

Following the procedure described in Example 1A, step 1, 4-isopropylbenzaldehyde and 4-isopropylaniline gave the title compound as a colorless oil.

$^1$H NMR (acetone-$d_6$) δ 7.32 (2H, d), 7.21 (2H, d), 6.98 (2H, d), 6.61 (2H, d), 5.22 (1H, br s), 4.29 (2H, d), 2.90 (1H, s), 2.76 (1H, m), 1.23 (6H, d), 1.17 (6H, d).

Step 2. (+/−)-N-(4-Isopropylbenzyl)-N-(4-isopropylphenyl)-2-methoxy-5,6,7,8-tetrahydroquinoline-8-carboxamide

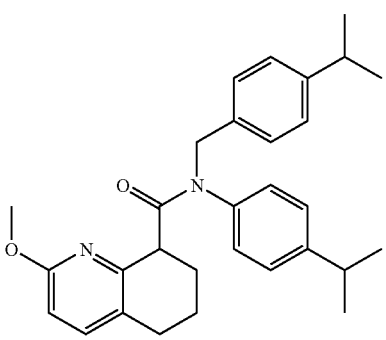

Following the procedure described in Example 1A, step 3, using 2-methoxy-5,6,7,8-tetrahydroquinoline, and (4-isopropylbenzyl)(4-isopropylphenyl)amine gave the title compound as a foam.

¹H NMR (acetone-d₆) δ 7.40 (2H, m), 7.33 (1H, d), 7.30-7.26 (4H, m), 7.16 (2H, d), 6.54 (1H, d), 5.30 (1H, d), 4.59 (1H, d), 3.90-3.85 (4H, m), 2.94-2.86 (2H, m), 2.71 (1H, m), 2.60 (1H, m), 2.09-2.03 (2H, m), 1.96 (1H, m), 1.47 (1H, m), 1.23 (6H, d), 1.22 (6H, d).

EXAMPLE 5

(+/−)-N-(Biphenyl-4-ylmethyl)-N-(4-isopropylphenyl)-2-methoxy-5,6,7,8-tetrahydroquinoline-8-carboxamide

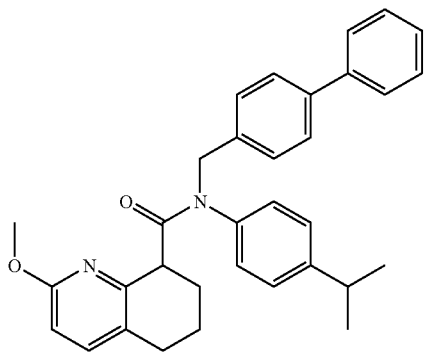

Step 1. N-(Biphenyl-4-ylmethyl)-4-isopropylaniline

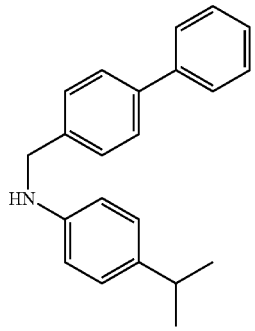

Following the procedure described in Example 1A, step 1, 4-biphenyl carboxaldehyde and 4-isopropylaniline gave the title compound as a white solid.

¹H NMR (acetone-d₆) δ 7.67 (2H, m), 7.63 (2H, d), 7.51 (2H, d), 7.46 (2H, t), 7.36 (1H, t), 6.99 (2H, d), 6.63 (2H, d), 5.37 (1H, br s), 4.40 (2H, d), 2.77 (1H, m), 1.17 (6H, d).

Step 2. (+/−)-N-(Biphenyl-4-ylmethyl)-N-(4-isopropylphenyl)-2-methoxy-5,6,7,8-tetrahydroquinoline-8-carboxamide

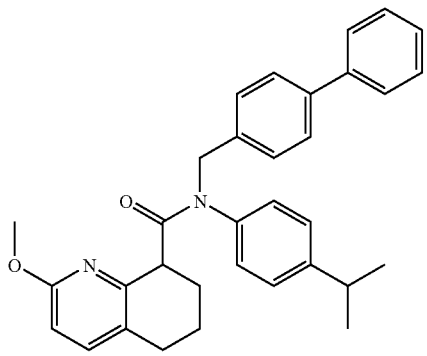

Following the procedure described in Example 1A, step 3, using 2-methoxy-5,6,7,8-tetrahydroquinoline, and N-(biphenyl-4-ylmethyl)-4-isopropylaniline gave the title compound as a colorless oil which gradually solidified.

¹H NMR (acetone-d₆) δ 7.66 (2H, d), 7.59 (2H, d), 7.48-7.44 (6H, m), 7.38-7.30 (4H, m), 6.55 (1H, d), 5.40 (1H, d), 4.68 (1H, d), 3.93-3.90 (4H, m), 2.95-2.90 (1H, m), 2.76-2.70 (1H, m), 2.62-2.57 (1H, m), 2.13-2.03 (2H, m), 2.00-1.97 (1H, m), 1.49-1.46 (1H, m), 1.22 (6H, d).

EXAMPLE 6

(+/−)-N-(4-isopropylphenyl)-2-methoxy-N-[4-(trifluoromethyl)benzyl]-5,6,7,8-tetrahydroquinoline-8-carboxamide

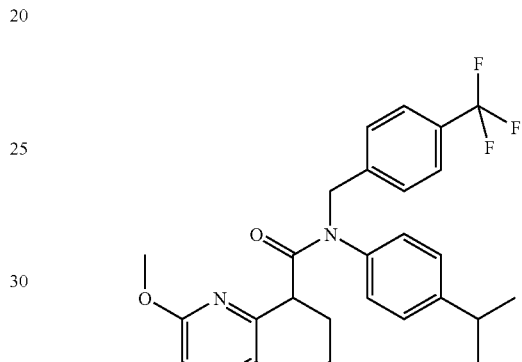

Step 1. (4-Isopropylphenyl)[4-(trifluoromethyl)benzyl]amine

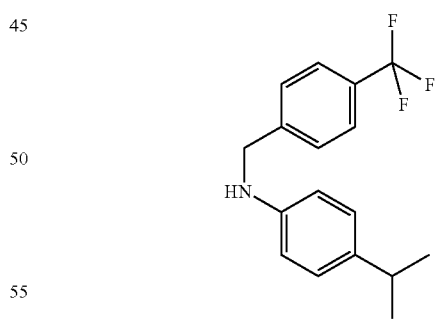

Following the procedure described in Example 1A, step 1, 4-(trifluoromethyl)benzaldehyde and 4-isopropylaniline gave the title compound as a pale yellow oil.

¹H NMR (acetone-d₆) δ 7.68 (2H, d), 7.64 (2H, d), 6.98 (2H, d), 6.58 (2H, d), 5.52 (1H, br s), 4.48 (2H, d), 2.79-2.73 (1H, m), 1.17 (6H, d).

Step 2. (+/−)-N-(4-isopropylphenyl)-2-methoxy-N-[4-(trifluoromethyl)benzyl]-5,6,7,8-tetrahydroquinoline-8-carboxamide

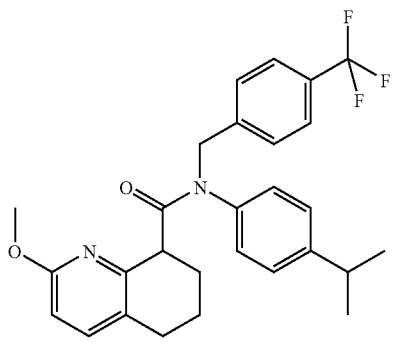

Following the procedure described in Example 1A, step 3, using 2-methoxy-5,6,7,8-tetrahydroquinoline, and (4-isopropylphenyl)[4-(trifluoromethyl)benzyl]amine gave the title compound as a foam.

$^1$H NMR (acetone-$d_6$) δ 7.65 (2H, d), 7.59 (2H, d), 7.44 (2H, d), 7.36-7.31 (3H, m), 6.56 (1H, d), 5.41 (1H, d), 4.77 (1H, d), 3.92-3.88 (4H, m), 2.96-2.90 (1H, m), 2.75-2.69 (1H, m), 2.63-2.58 (1H, m), 2.11-1.97 (3H, m), 1.50-1.46 (1H, m), 1.22 (6H, d).

EXAMPLE 7

(+/−)-N-(4-Isopropylphenyl)-2-methoxy-N-(4-methoxybenzyl)-5,6,7,8-tetrahydroquinoline-8-carboxamide

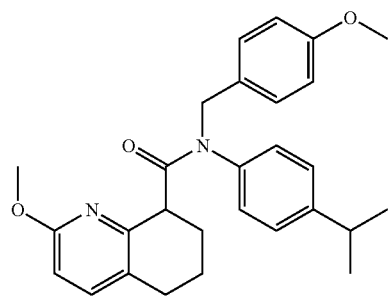

Step 1. (4-Isopropylphenyl)(4-methoxybenzyl)amine

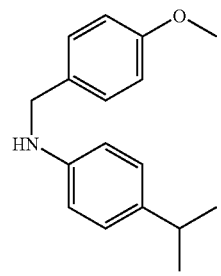

Following the procedure described in Example 1A, step 1, 4-methoxybenzaldehyde and 4-isopropylaniline gave the title compound as a foam.

$^1$H NMR (acetone-$d_6$) δ 7.29 (2H, d), 6.95 (2H, d), 6.86 (2H, d), 6.57 (2H, d), 5.16 (1H, br s), 4.23 (2H, d), 3.75 (3H, s), 2.73 (1H, sept), 1.14 (6H, d).

Step 2. (+/−)-N-(4-Isopropylphenyl)-2-methoxy-N-(4-methoxybenzyl)-5,6,7,8-tetrahydroquinoline-8-carboxamide

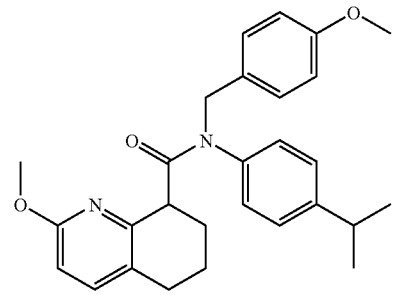

Following the procedure described in Example 1A, step 3, using 2-methoxy-5,6,7,8-tetrahydroquinoline, and (4-isopropylphenyl)(4-methoxybenzyl)amine gave the title compound as a foam.

$^1$H NMR (acetone-$d_6$) δ 7.37-7.33 (3H, m), 7.29 (2H, d), 7.24 (2H, d), 6.84 (2H, d), 6.54 (1H, d), 5.26 (1H, d), 4.55 (1H, d), 3.89-3.83 (4H, m), 3.78 (3H, s), 2.92 (1H, sept), 2.75-2.69 (1H, m), 2.62-2.57 (1H, m), 2.09-2.03 (2H, m), 1.98-1.94 (1H, m), 1.50-1.43 (1H, m), 1.23 (6H, d).

EXAMPLE 8

(+/−)-N-(4-Isopropylphenyl)-2-methoxy-N-(3-methoxybenzyl)-5,6,7,8-tetrahydroquinoline-8-carboxamide

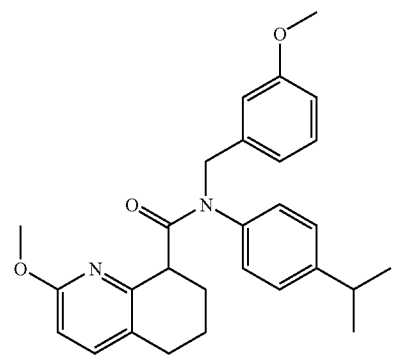

Step 1. (4-Isopropylphenyl)(3-methoxybenzyl)amine

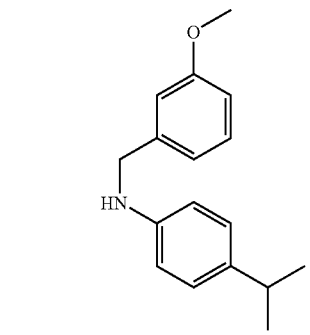

Following the procedure described in Example 1A, step 1, 3-methoxybenzaldehyde and 4-isopropylaniline gave the title compound as a pale yellow oil.

$^1$H NMR (acetone-$d_6$) δ 7.24 (1H, t), 7.00-6.97 (4H, m), 6.81 (1H, dd), 6.60 (2H, d), 5.29 (1H, br s), 4.32 (2H, d), 3.78 (3H, s), 2.80-2.73 (1H, m), 1.17 (6H, d).

Step 2. (+/−)-N-(4-Isopropylphenyl)-2-methoxy-N-(3-methoxybenzyl)-5,6,7,8-tetrahydroquinoline-8-carboxamide

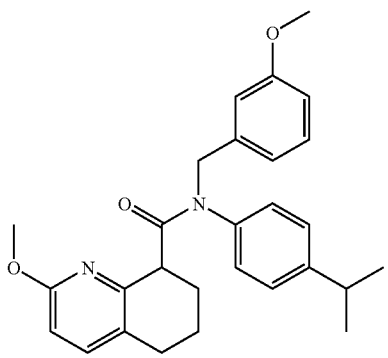

Following the procedure described in Example 1A, step 3, using 2-methoxy-5,6,7,8-tetrahydroquinoline, and (4-isopropylphenyl)(3-methoxybenzyl)amine gave the title compound as a colorless oil.

$^1$H NMR (acetone-d$_6$) δ 7.41 (2H, m), 7.34 (1H, d), 7.30 (2H, m), 7.20 (1H, t), 6.92 (2H, m), 6.81 (1H, dd), 6.54 (1H, d), 5.28 (1H, d), 4.64 (1H, d), 3.91-3.88 (4H, m), 3.74 (3H, s), 2.95-2.90 (1H, sept), 2.75-2.69 (1H, m), 2.62-2.57 (1H, m), 2.11-2.02 (2H, m), 1.98-1.94 (1H, m), 1.51-1.46 (1H, m), 1.23 (6H, d).

EXAMPLE 9

(+/−)-N-(4-Isopropylphenyl)-2-methoxy-N-[4-(methylthio)benzyl]-5,6,7,8-tetrahydroquinoline-8-carboxamide

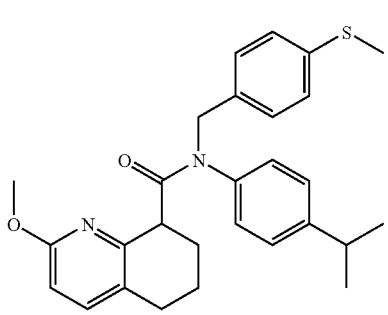

Step 1. (4-Isopropylphenyl)[4-(methylthio)benzyl] amine

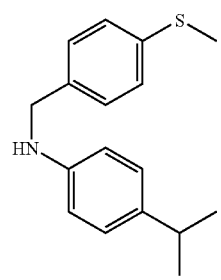

Following the procedure described in Example 1A, step 1, 4-(methylthio)benzaldehyde and 4-isopropylaniline gave the title compound as an off-white solid.

$^1$H NMR (acetone-d$_6$) δ 7.35 (2H, d), 7.25 (2H, d), 6.95 (2H, d), 6.60 (2H, d), 5.25 (1H, br s), 4.30 (2H, d), 2.85 (1H, m), 2.50 (3H, s), 1.17 (6H, d).

Step 2. (+/−)-N-(4-Isopropylphenyl)-2-methoxy-N-[4-(methylthio)benzyl]-5,6,7,8-tetrahydroquinoline-8-carboxamide

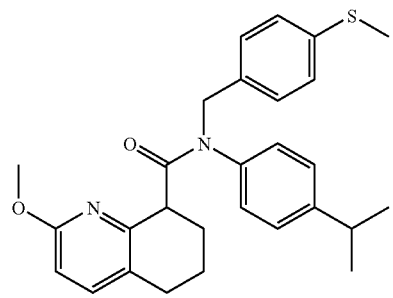

Following the procedure described in Example 1A, step 3, using 2-methoxy-5,6,7,8-tetrahydroquinoline, and (4-isopropylphenyl)[4-(methylthio)benzyl]amine gave the title compound as an off-white solid $^1$H NMR (acetone-d$_6$) δ 7.50 (9H, m), 6.60 (1H, d), 5.30 (1H, d), 4.60 (1H, d), 3.90 (3H, s), 3.85 (1H, m), 3.00-1.50 (7H, m), 2.50 (3H, s), 1.20 (6H, d).

EXAMPLE 10

(+/−)-N-(4-Isopropylphenyl)-2-methoxy-N-[4-(methylsulfonyl)benzyl]-5,6,7,8-tetrahydroquinoline-8-carboxamide

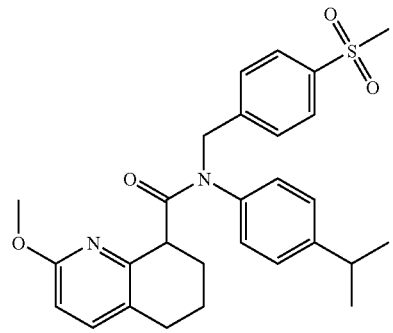

To a 0.023 M solution of (+/−)-N-(4-isopropylphenyl)-2-methoxy-N-[4-(methylthio)benzyl]-5,6,7,8-tetrahydroquinoline-8-carboxamide in MeOH was added 3.1 equiv of Na$_2$WO$_4$.2H$_2$O and 6.3 equiv. of H$_2$O$_2$ 30%. After a period of 1 h at room temperature, the reaction mixture was partitioned between EtOAc and aqueous saturated NaHCO$_3$. The organic phase was separated, washed with aqueous Na$_2$S$_2$O$_3$, dried over anhydrous Na$_2$SO$_4$, filtered and concentrated. The crude material was further purified by flash chromatography, eluting with 100% EtOAc to provide the title compound as a yellow compound.

$^1$H NMR (acetone-d$_6$) δ 7.50 (9H, m), 6.60 (1H, d), 5.30 (1H, d), 4.60 (1H, d), 3.90 (3H, s), 3.85 (3H, s), 3.00-1.50 (7H, m), 2.50 (3H, s), 1.20 (6H, d).

EXAMPLE 11

(+/−)-N-[4-(Difluoromethoxy)benzyl]-N-(4-isopropylphenyl)-2-methoxy-5,6,7,8-tetrahydroquinoline-8-carboxamide

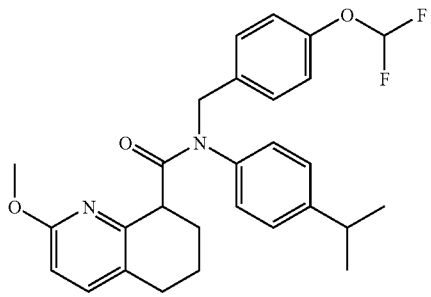

Step 1.
N-[4-(Difluoromethoxy)benzyl]-4-isopropylaniline

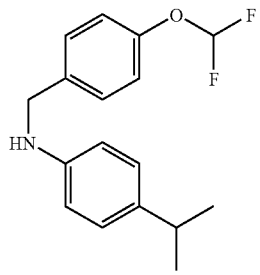

Following the procedure described in Example 1A, step 1, 4-(difluoromethoxy)benzaldehyde and 4-isopropylaniline gave the title compound as a pale yellow oil.

$^1$H NMR (acetone-$d_6$) δ 7.46 (2H, d), 7.14 (2H, d), 6.98 (2H, d), 6.97 (1H, t), 6.59 (2H, d), 5.36 (1H, br s), 4.35 (2H, d), 2.79-2.73 (1H, m), 1.17 (6H, d).

Step 2. (+/−)-N-[4-(Difluoromethoxy)benzyl]-N-(4-isopropylphenyl)-2-methoxy-5,6,7,8-tetrahydroquinoline-8-carboxamide

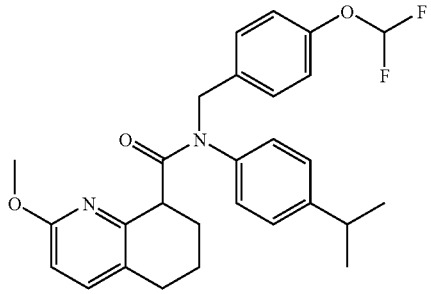

Following the procedure described in Example 1A, step 3, using 2-methoxy-5,6,7,8-tetrahydroquinoline, and N-[4-(difluoromethoxy)benzyl]4-isopropylaniline gave the title compound as a white solid.

$^1$H NMR (acetone-$d_6$) δ 7.41-7.39 (4H, m), 7.35-7.30 (3H, m), 7.11 (2H, d), 6.99 (1H, t), 6.55 (1H, d), 5.33 (1H, d), 4.62 (1H, d), 3.89-3.88 (4H, m), 2.93 (1H, m), 2.75-2.69 (1H, m, sept), 2.62-2.57 (1H, m), 2.10-2.02 (2H, m), 1.99-1.95 (1H, m), 1.49-1.45 (1H, m), 1.23 (6H, d).

EXAMPLE 12

(+/−)-N-(4-Isopropylphenyl)-2-methoxy-N-[4-(trifluoromethoxy)benzyl]-5,6,7,8-tetrahydroquinoline-8-carboxamide

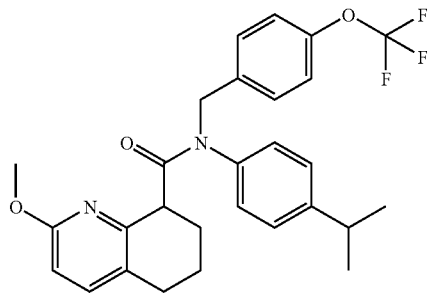

Step 1. (4-Isopropylphenyl)[4-(trifluoromethoxy)benzyl]amine

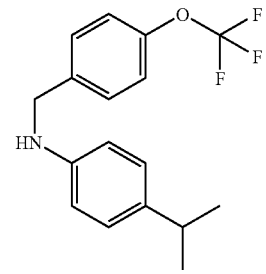

Following the procedure described in Example 1A, step 1, 4-(trifluoromethoxy)benzaldehyde and 4-isopropylaniline gave the title compound as a colorless oil.

$^1$H NMR (acetone-$d_6$) δ 7.54 (2H, d), 7.30 (2H, d), 6.99 (2H, d), 6.60 (2H, d), 5.42 (1H, br s), 4.40 (2H, d), 2.79-2.73 (1H, m), 1.17 (6H, d).

Step 2. (+/−)-N-(4-Isopropylphenyl)-2-methoxy-N-[4-(trifluoromethoxy)benzyl]-5,6,7,8-tetrahydroquinoline-8-carboxamide

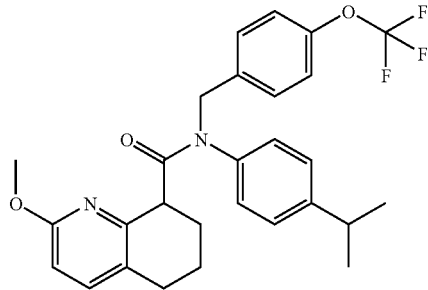

Following the procedure described in Example 1A, step 3, using 2-methoxy-5,6,7,8-tetrahydroquinoline, and (4-isopropylphenyl)[4-(trifluoromethoxy)benzyl]amine gave the title compound as a colorless oil.

$^1$H NMR (acetone-$d_6$) δ 7.48 (2H, d), 7.42-7.41 (2H, m), 7.35-7.31 (3H, m), 7.27 (2H, d), 6.55 (1H, d), 5.37 (1H, d), 4.65 (1H, d), 3.90-3.86 (4H, m), 2.93 (1H, m), 2.75-2.69 (1H, m), 2.62-2.57 (1H, m), 2.10-1.96 (3H, m), 1.49-1.46 (1H, m), 1.23 (6H, d).

EXAMPLE 13

(+/−)-N-(4-Isopropoxybenzyl)-N-(4-isopropylphenyl)-2-methoxy-5,6,7,8-tetrahydroquinoline-8-carboxamide

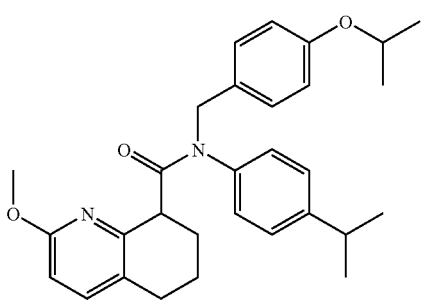

Step 1. N-(4-Isopropoxybenzyl)-4-isopropylaniline

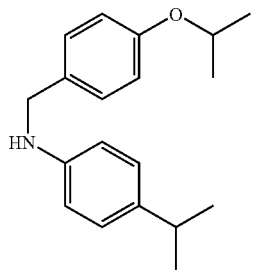

Following the procedure described in Example 1A, step 1, 4-isopropoxybenzaldehyde and 4-isopropylaniline gave the title compound as an off-white solid.

$^1$H NMR (acetone-d$_6$) δ 7.30 (2H, d), 6.98 (2H, d), 6.87 (2H, d), 6.61 (2H, d), 5.15 (1H, br s), 4.60 (1H, sept), 4.24 (2H, d), 2.79-2.73 (1H, m), 1.30 (6H, d), 1.17 (6H, d).

Step 2. (+/−)-N-(4-Isopropoxybenzyl)-N-(4-isopropylphenyl)-2-methoxy-5,6,7,8-tetrahydroquinoline-8-carboxamide

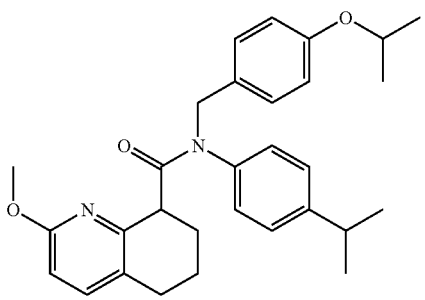

Following the procedure described in Example 1A, step 3, using 2-methoxy-5,6,7,8-tetrahydroquinoline, and N-(4-isopropoxybenzyl)-4-isopropylaniline gave the title compound as a foam.

$^1$H NMR (acetone-d$_6$) δ 7.37-7.33 (3H, m), 7.29 (2H, d), 7.22 (2H, d), 6.82 (2H, d), 6.54 (1H, d), 5.26 (1H, d), 4.62-4.57 (1H, m), 4.53 (1H, d), 3.87-3.83 (4H, m), 2.95-2.90 (1H, m), 2.75-2.69 (1H, m), 2.62-2.57 (1H, m), 2.10-2.04 (2H, m), 1.97-1.94 (1H, m), 1.49-1.46 (1H, m), 1.30 (6H, d), 1.23 (6H, d).

EXAMPLE 14

(+/−)-N-[4-(Dimethylamino)benzyl]-N-(4-isopropylphenyl)-2-methyl-5,6,7,8-tetrahydroquinoline-8-carboxamide

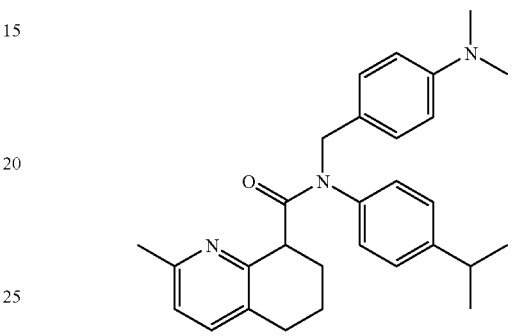

Following the procedure described in Example 1A, step 3, using 2-methyl-5,6,7,8-tetrahydroquinoline, and N-[4-(dimethylamino)benzyl]4-isopropylaniline gave the title compound as a white solid.

$^1$H NMR (acetone-d$_6$) δ 7.39 (2H, m), 7.31 (1H, d), 7.25-7.23 (4H, m), 6.99 (1H, d), 6.70 (2H, d), 5.22 (1H, d), 4.53 (1H, d), 3.90-3.87 (1H, m), 2.92-2.88 (7H, m), 2.80-2.74 (1H, m), 2.68-2.63 (1H, m), 2.52 (3H, s), 2.11-1.94 (3H, m), 1.50-1.47 (1H, m), 1.22 (6H, d).

EXAMPLE 15

(+/−)-N-[4-(Dimethylamino)benzyl]-2-isopropyl-N-(4-isopropylphenyl)-5,6,7,8-tetrahydroquinoline-8-carboxamide

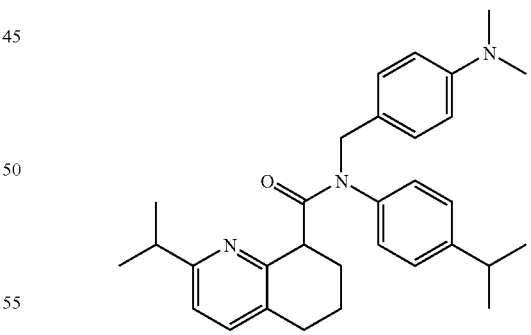

Step 1. 2-Ethylquinoline

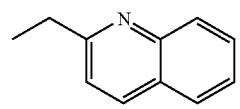

To a 0.40 M solution of diisopropyl amine in THF at −10° C. was added slowly 1.0 equiv of a solution of n-BuLi (2.5 M/hexane). After 10 min, the mixture was cooled to −78° C. and 0.9 equiv of quinaldine was added dropwise. The red/orange solution was then stirred at 0° C. for 1 h. MeI was then added and the reaction was stirred at room temperature for 2 h. The reaction was quenched with aqueous $NH_4Cl$ solution, and then extracted with EtOAc. The organic phase was washed with $H_2O$ and brine. The solution was then dried ($MgSO_4$), filtered, and evaporated. The crude material was purified by flash chromatography with 1:10 EtOAc:hexanes to give the title compound as a pale yellow oil.

$^1$H NMR (acetone-$d_6$) δ 8.20 (1H, d), 7.95 (1H, d), 7.85 (1H, d), 7.70 (1H, t), 7.50 (1H, t), 7.40 (1H, d), 2.95 (2H, q), 1.35 (3H, t).

Step 2. 2-Isopropylquinoline

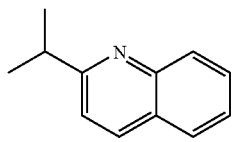

Following the procedure described in Example 15, step 1,2-ethylquinoline and MeI gave the title compound as a tan colored oil.

$^1$H NMR (acetone-$d_6$) δ 8.25 (1H, d), 8.00 (1H, d), 7.90 (1H, d), 7.70 (1H, t), 7.55 (1H, t), 7.45 (1H, d), 3.25 (1H, sept), 1.40 (6H, d).

Step 3. 2-Isopropyl-5,6,7,8-tetrahydroquinoline

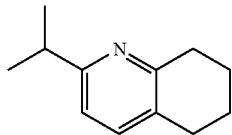

To a 0.23 M solution of 2-isopropylquinoline in trifluoroacetic acid in a Parr flask was added 0.1 equiv of $PtO_2$. The suspension was set up on the Parr apparatus at 44 psi $H_2$ overnight. After removal of the $H_2$, $CH_2Cl_2$ was added, and the suspension was filtered through Celite. The solvent was removed under vacuum, and the residue was partitioned between EtOAc and saturated $NaHCO_3$ solution. The organic layer was washed with $H_2O$ and brine, and was then dried over anhydrous $MgSO_4$, filtered and evaporated to give the title compound as a tan colored oil.

$^1$H NMR (acetone-$d_6$) δ 7.35 (1H, d), 6.95 (1H, d), 3.00-2.90 (1H, m), 2.80 (2H, m), 2.70 (2H, m), 1.90 (2H, m), 1.80 (2H, m), 1.25 (6H, m).

Step 4. (+/−)-N-[4-(Dimethylamino)benzyl]-2-isopropyl-N-(4-isopropylphenyl)-5,6,7,8-tetrahydroquinoline-8-carboxamide

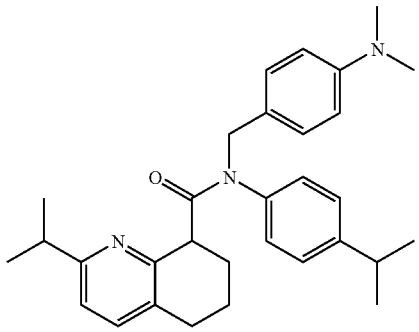

Following the procedure described in Example 1A, step 3, using 2-isopropyl-5,6,7,8-tetrahydroquinoline, and N-(4-dimethylaminobenzyl)-4-isopropylaniline gave the title compound as a foam.

$^1$H NMR (acetone-$d_6$) δ 7.49-7.40 (2H, m), 7.33 (1H, d), 7.28-7.19 (4H, m), 7.01 (1H, d), 6.70-6.63 (2H, m), 5.30 (1H, d), 4.46 (1H, d), 3.94-3.89 (1H, m), 3.09-3.02 (1H, m), 2.95-2.87 (7H, m), 2.82-2.74 (1H, m), 2.68-2.62 (1H, m), 2.16-2.01 (2H, m), 2.00-1.92 (1H, m), 1.51-1.44 (1H, m), 1.33 (6H, d), 1.22 (6H, d).

EXAMPLE 16

(+/−)-N-[4-(Dimethylamino)benzyl]-2-ethoxy-N-(4-isopropylphenyl)-5,6,7,8-tetrahydroquinoline-8-carboxamide

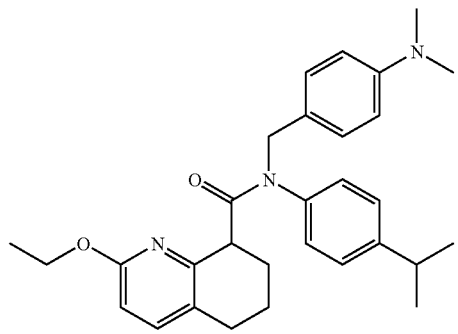

Step 1. 2-Ethoxy-5,6,7,8-tetrahydroquinoline

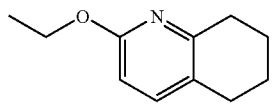

Following the procedure described in Example 1A, step 2, 5,6,7,8-tetrahydroquinolin-2 (1H)-one and EtI gave the title compound as a pale yellow oil.

$^1$H NMR (acetone-$d_6$) δ 7.42 (1H, d), 6.58 (1H, d), 4.39 (2H, q), 2.85-2.82 (2H, m), 2.78-2.76 (2H, m), 1.97-1.93 (2H, m), 1.90-1.86 (2H, m), 1.43 (3H, t).

Step 2. (+/−)-N-[4-(Dimethylamino)benzyl]-2-ethoxy-N-(4-isopropylphenyl)-5,6,7,8-tetrahydroquinoline-8-carboxamide

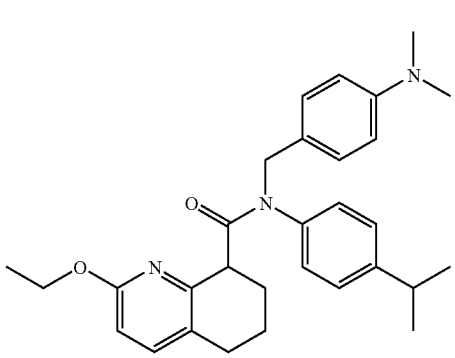

Following the procedure described in Example 1A, step 3, using 2-ethoxy-5,6,7,8-tetrahydroquinoline, and N-(4-dimethylaminobenzyl)-4-isopropylaniline gave the title compound as a waxy oil.

$^1$H NMR (acetone-$d_6$) δ 7.34-7.24 (5H, m), 7.14 (2H, d), 6.65 (2H, d), 6.50 (1H, d), 5.22 (1H, d), 4.48 (1H, d), 4.37-4.26 (2H, m), 3.83-3.80 (1H, m), 2.94-2.86 (7H, m), 2.73-2.67 (1H, m), 2.59-2.54 (1H, m), 2.10-1.92 (3H, m), 1.47-1.40 (1H, m), 1.36 (3H, t), 1.23 (6H, d).

EXAMPLE 17

(+/−)-N-[4-(Dimethylamino)benzyl]-2-isopropoxy-N-(4-isopropylphenyl)-5,6,7,8-tetrahydroquinoline-8-carboxamide

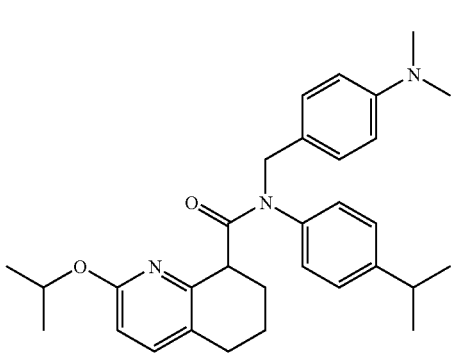

Step 1. 2-Isopropoxy-5,6,7,8-tetrahydroquinoline

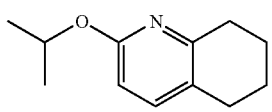

Following the procedure described in Example 1A, step 2, 5,6,7,8-tetrahydroquinolin-2(1H)-one and i-PrI gave the title compound as a pale yellow oil.

$^1$H NMR (acetone-$d_6$) δ 7.26 (1H, d), 6.39 (1H, d), 5.27-5.24 (1H, m), 2.69-2.68 (2H, m), 2.64-2.61 (2H, d), 1.81-1.74 (4H, m), 1.25 (6H, d).

Step 2. (+/−)-N-[4-(Dimethylamino)benzyl]-2-isopropoxy-N-(4-isopropylphenyl)-5,6,7,8-tetrahydroquinoline-8-carboxamide

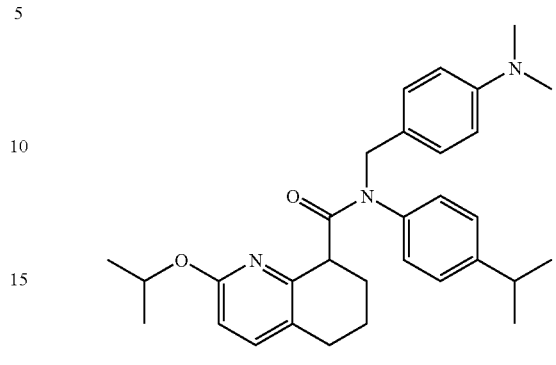

Following the procedure described in Example 1A, step 3, using 2-isopropoxy-5,6,7,8-tetrahydroquinoline, and N-(4-dimethylaminobenzyl)-4-isopropylaniline gave the title compound as a yellow oil.

$^1$H NMR (acetone-$d_6$) δ 7.31-7.25 (5H, m), 7.13 (2H, d), 6.66 (2H, d), 6.46 (1H, d), 5.30 (1H, sept), 5.14 (1H, d), 4.56 (1H, d), 3.82-3.80 (1H, m), 2.95-2.89 (7H, m), 2.73-2.67 (1H, m), 2.59-2.54 (1H, m), 2.08-2.00 (2H, m), 1.96-1.92 (1H, m), 1.48-1.40 (1H, m), 1.37 (3H, d), 1.31 (3H, d), 1.23 (6H, d).

EXAMPLE 18

(+/−)-N-[4-(Dimethylamino)benzyl]-N-(4-isopropylphenyl)-2-(methylthio)-5,6,7,8-tetrahydroquinoline-8-carboxamide

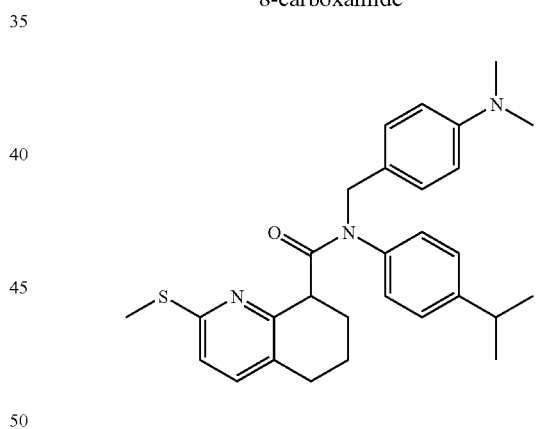

Step 1. 2-(Methylthio)-5,6,7,8-tetrahydroquinoline

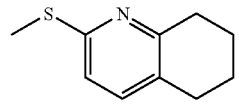

To a 0.20 M solution of 2-chloro-5,6,7,8-tetrahydroquinoline in NMP was added 1.5 equiv of NaSMe. After a period of 15 min at 100° C., the reaction mixture was partitioned between EtOAc and H$_2$O. The organic layer was separated, dried over anhydrous Na$_2$SO$_4$, filtered and concentrated. The crude material was further purified by flash chromatography eluting with 10% EtOAc in hexanes to provide the title compound as a yellow compound.

$^1$H NMR (acetone-$d_6$) δ 7.25 (1H, d), 6.95 (1H, d), 2.85 (2H, m), 2.70 (2H, m), 2.50 (3H, s), 1.85 (2H, m), 1.75 (2H, m).

Step 2. (+/−)-N-[4-(Dimethylamino)benzyl]-N-(4-isopropylphenyl)-2-(methylthio)-5,6,7,8-tetrahydroquinoline-8-carboxamide

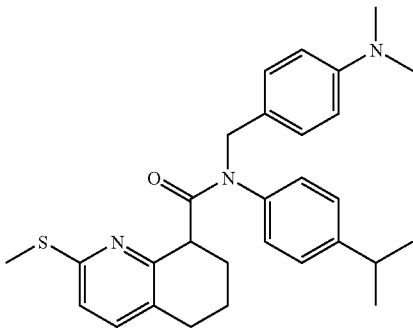

Following the procedure described in Example 1A, step 3, using 2-(methylthio)-5,6,7,8-tetrahydroquinoline, and N-(4-dimethylaminobenzyl)-4-isopropylaniline gave the title compound as a yellow compound.

$^1$H NMR (acetone-$d_6$) δ 7.30 (5H, m), 7.15 (2H, d), 7.00 (1H, d), 6.80 (2H, d), 5.10 (1H, d), 4.50 (1H, d), 3.85 (1H, m), 2.90 (6H, s), 3.00-1.50 (7H, m) 2.50 (3H, s), 1.20 (6H, d).

What is claimed is:

1. A compound of formula II

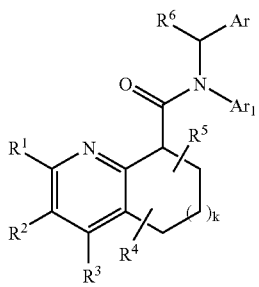

or a pharmaceutically acceptable salt thereof wherein:
$R^1$ is selected from the group consisting of
  (1) —$C_{1-3}$alkyl,
  (2) —$OC_{1-3}$alkyl,
  (3) —$SC_{1-3}$alkyl, and
  (4) —$C_{2-4}$alkenyl;
wherein definitions (1) to (4) are optionally substituted with 1, 2 or 3 substituents selected from the group consisting of halo, hydroxyl, —CN, —$NO_2$, and $NH_2$;
$R^2$ and $R^3$ are each hydrogen;
$R^4$ and $R^5$ are each hydrogen;
$R^6$ is hydrogen;
k is 1, and
Ar and $Ar_1$ are each independently an phenyl or pyridyl, optionally substituted with 1, 2, or 3 substitents selected from
  (1) -halo,
  (2) $C_{1-4}$alkyl, optionally substituted with 1, 2, 3 or 4 halo groups,
  (3) —$NR^7R^8$,
  (4) phenyl,
  (5) —$OC_{1-4}$alkyl, optionally substituted with 1, 2, 3 or 4 halo groups,
  (6) —$SC_{1-4}$alkyl; and
$R^7$ and $R^8$ are each independently hydrogen or methyl.

2. A compound selected from the group consisting of:
(+)-N-[4-(Dimethylamino)benzyl]-N-(4-isopropylphenyl)-2-methoxy-5,6,7,8-tetrahydroquinoline-8-carboxamide, Enantiomer A,
(−)-N-[4-(Dimethylamino)benzyl]-N-(4-isopropylphenyl)-2-methoxy-5,6,7,8-tetrahydroquinoline-8-carboxamide, Enantiomer A,
(+)-N-[4-(Dimethylamino)benzyl]-N-(4-isopropylphenyl)-2-methoxy-5,6,7,8-tetrahydroquinoline-8-carboxamide, Enantiomer B,
(−)-N-[4-(Dimethylamino)benzyl]-N-(4-isopropylphenyl)-2-methoxy-5,6,7,8-tetrahydroquinoline-8-carboxamide, Enantiomer B,
(+/−)-N-(4-Chlorobenzyl)-N-(4-isopropylphenyl)-2-methoxy-5,6,7,8-tetrahydroquinoline-8-carboxamide,
(+/−)-N-(4-Isopropylbenzyl)-N-(4-isopropylphenyl)-2-methoxy-5,6,7,8-tetrahydroquinoline-8-carboxamide,
(+/−)-N-(Biphenyl-4-ylmethyl)-N-(4-isopropylphenyl)-2-methoxy-5,6,7,8-tetrahydroquinoline-8-carboxamide,
(+/−)-N-(4-isopropylphenyl)-2-methoxy-N-[4-(trifluoromethyl)benzyl]-5,6,7,8-tetrahydroquinoline-8-carboxamide,
(+/−)-N-(4-Isopropylphenyl)-2-methoxy-N-(4-methoxybenzyl)-5,6,7,8-tetrahydroquinoline-8-carboxamide,
(+/−)-N-(4-Isopropylphenyl)-2-methoxy-N-(3-methoxybenzyl)-5,6,7,8-tetrahydroquinoline-8-carboxamide,
(+/−)-N-(4-Isopropylphenyl)-2-methoxy-N-[4-(methylthio)benzyl]-5,6,7,8-tetrahydroquinoline-8-carboxamide,
(+/−)-N-(4-Isopropylphenyl)-2-methoxy-N-[4-(methylsulfonyl)benzyl]-5,6,7,8-tetrahydroquinoline-8-carboxamide,
(+/−)-N-[4-(Difluoromethoxy)benzyl]-N-(4-isopropylphenyl)-2-methoxy-5,6,7,8-tetrahydroquinoline-8-carboxamide,
(+/−)-N-(4-Isopropoxybenzyl)-N-(4-isopropylphenyl)-2-methoxy-5,6,7,8-tetrahydroquinoline-8-carboxamide,
(+/−)-N-[4-(Dimethylamino)benzyl]-N-(4-isopropylphenyl)-2-methyl-5,6,7,8-tetrahydroquinoline-8-carboxamide,
(+/−)-N-[4-(Dimethylamino)benzyl]-2-isopropyl-N-(4-isopropylphenyl)-5,6,7,8-tetrahydroquinoline-8-carboxamide,
(+/−)-N-[4-(Dimethylamino)benzyl]-2-ethoxy-N-(4-isopropylphenyl)-5,6,7,8-tetrahydroquinoline-8-carboxamide,
(+/−)-N-[4-(Dimethylamino)benzyl]-2-isopropoxy-N-(4-isopropylphenyl)-5,6,7,8-tetrahydroquinoline-8-carboxamide, and
(+/−)-N-[4-(Dimethylamino)benzyl]-N-(4-isopropylphenyl)-2-(methylthio)-5,6,7,8-tetrahydroquinoline-8-carboxamide, or a pharmaceutically acceptable salt thereof.

3. A pharmaceutical composition comprising a compound according to claim 1 or a pharmaceutically acceptable salt thereof; and a pharmaceutically acceptable carrier.

4. A compound according to claim 1 wherein Ar and Ar1 are each optionally substituted phenyl.

5. A pharmaceutical composition comprising a compound according to claim 2 or a pharmaceutically acceptable salt thereof; and a pharmaceutically acceptable carrier.

* * * * *